(12) United States Patent
Chen et al.

(10) Patent No.: US 10,330,608 B2
(45) Date of Patent: Jun. 25, 2019

(54) SYSTEMS AND METHODS FOR WAFER SURFACE FEATURE DETECTION, CLASSIFICATION AND QUANTIFICATION WITH WAFER GEOMETRY METROLOGY TOOLS

(75) Inventors: Haiguang Chen, Mountain View, CA (US); Jaydeep K. Sinha, Livermore, CA (US); Sergey Kamensky, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1525 days.

(21) Appl. No.: 13/469,339

(22) Filed: May 11, 2012

(65) Prior Publication Data

US 2013/0304399 A1    Nov. 14, 2013

(51) Int. Cl.
| | |
|---|---|
| *G01N 21/95* | (2006.01) |
| *H01L 21/66* | (2006.01) |
| *G06T 7/00* | (2017.01) |
| *G01N 21/88* | (2006.01) |
| *G01N 21/956* | (2006.01) |
| *G06T 7/12* | (2017.01) |
| *G06T 7/62* | (2017.01) |
| *G01B 11/02* | (2006.01) |

(52) U.S. Cl.
CPC ..... *G01N 21/9501* (2013.01); *G01N 21/8851* (2013.01); *G01N 21/956* (2013.01); *G06T 7/0004* (2013.01); *G06T 7/12* (2017.01); *G06T 7/62* (2017.01); *H01L 22/12* (2013.01); *H01L 22/20* (2013.01); *G01B 11/02* (2013.01); *G01N 2021/8864* (2013.01); *G06T 2207/30148* (2013.01); *H01L 2924/0002* (2013.01)

(58) Field of Classification Search
CPC ..... G06T 7/0004; G06T 7/0083; G06T 7/602; H01L 22/12
USPC ............................................................ 702/40
See application file for complete search history.

(56) References Cited

U.S. PATENT DOCUMENTS

| | | | | |
|---|---|---|---|---|
| 5,270,222 | A * | 12/1993 | Moslehi ............... | B24B 37/013 257/E21.525 |
| 6,292,582 | B1 * | 9/2001 | Lin et al. ...................... | 382/149 |
| 7,201,799 | B1 | 4/2007 | Velidandla | |
| 7,272,459 | B2 * | 9/2007 | Kokotov ................ | G05B 11/32 700/52 |
| 7,372,583 | B1 * | 5/2008 | Jin ...................... | G03F 7/70491 356/601 |

(Continued)

FOREIGN PATENT DOCUMENTS

| | | |
|---|---|---|
| JP | H09-186208 | 2/1999 |
| JP | 2002267616 A | 9/2002 |

(Continued)

*Primary Examiner* — Ricky Ngon
(74) *Attorney, Agent, or Firm* — Suiter Swantz pc llo

(57) ABSTRACT

Systems and methods for providing micro defect inspection capabilities for optical systems such as wafer metrology tools and interferometer systems are disclosed. The systems and methods in accordance with the present disclosure may detect, classify and quantify wafer surface features, wherein the detected defects are classified and the important defect metrology information of height/depth, area and volume is reported. The systems and methods in accordance with the present disclosure therefore provide more values for quantifying the negative effect of these defects on the wafer quality.

25 Claims, 18 Drawing Sheets

(56) References Cited

U.S. PATENT DOCUMENTS

| | | | |
|---|---|---|---|
| 7,373,277 B1 | 5/2008 | Wu et al. | |
| 7,711,521 B1 | 5/2010 | Wu et al. | |
| 2002/0176074 A1* | 11/2002 | Hasan | G01N 21/9501 356/237.5 |
| 2003/0046321 A1* | 3/2003 | Raymond | G06T 5/20 708/300 |
| 2003/0164942 A1 | 9/2003 | Take | |
| 2004/0036863 A1* | 2/2004 | Matsusita | G01N 21/956 356/237.2 |
| 2004/0105093 A1* | 6/2004 | Hamamatsu et al. | 356/237.4 |
| 2005/0080572 A1* | 4/2005 | Lin | G05B 19/41875 702/35 |
| 2007/0201032 A1* | 8/2007 | Ishimori | 356/485 |
| 2008/0298670 A1* | 12/2008 | Nakagaki et al. | 382/149 |
| 2009/0116727 A1* | 5/2009 | Jin et al. | 382/149 |
| 2010/0017010 A1* | 1/2010 | Cote | G05B 19/4184 700/110 |
| 2010/0067780 A1 | 3/2010 | Kawaragi | |
| 2013/0279791 A1* | 10/2013 | Kaizerman | G06T 7/0004 382/145 |

FOREIGN PATENT DOCUMENTS

| | | |
|---|---|---|
| JP | 2006005164 A | 1/2006 |
| JP | 2006105919 A | 4/2006 |
| JP | 2009535609 A | 10/2009 |
| WO | 2011085019 A2 | 7/2011 |

* cited by examiner

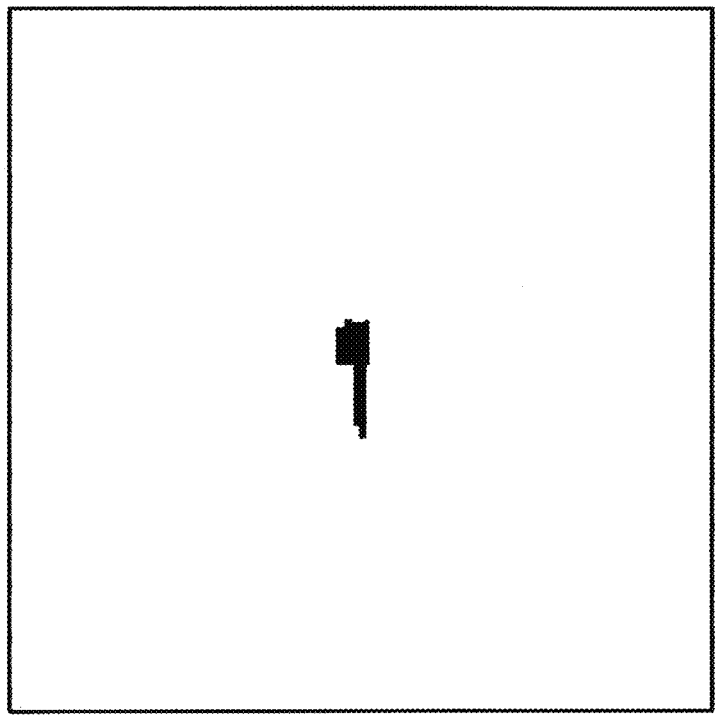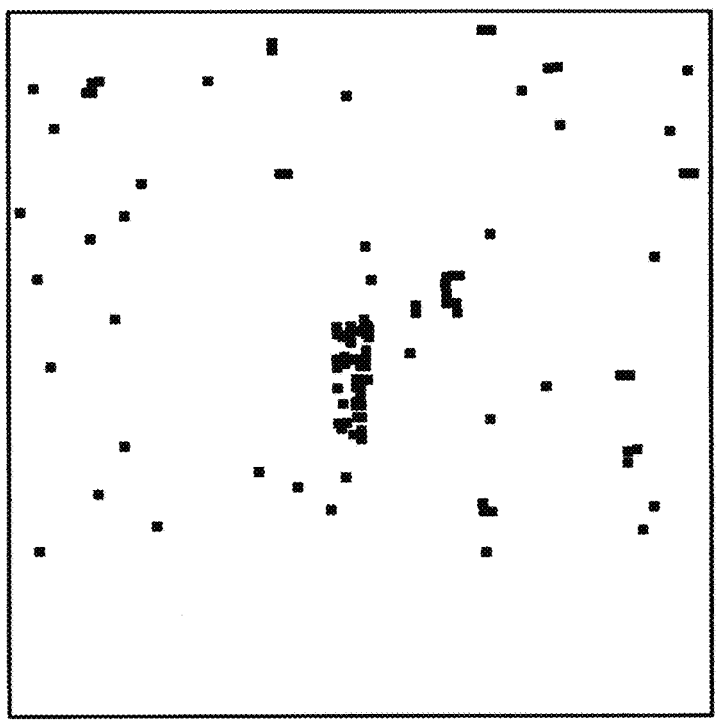
FIG. 11

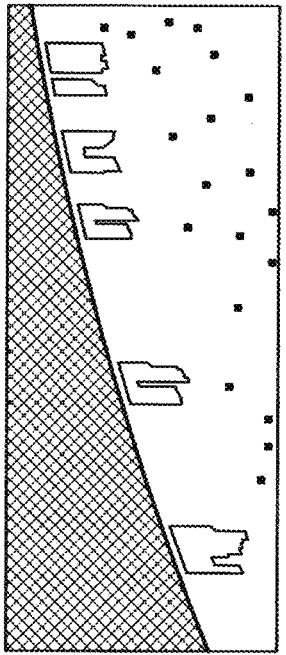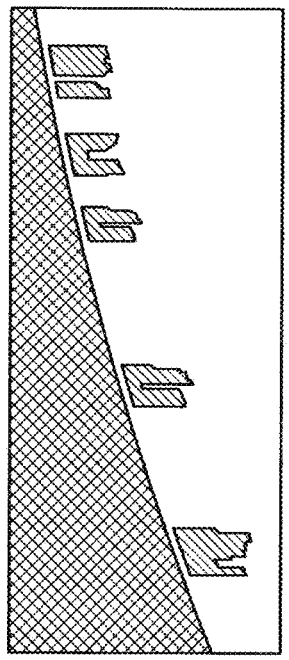
FIG. 12
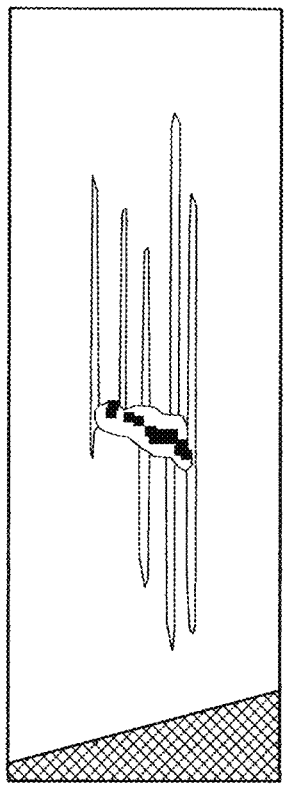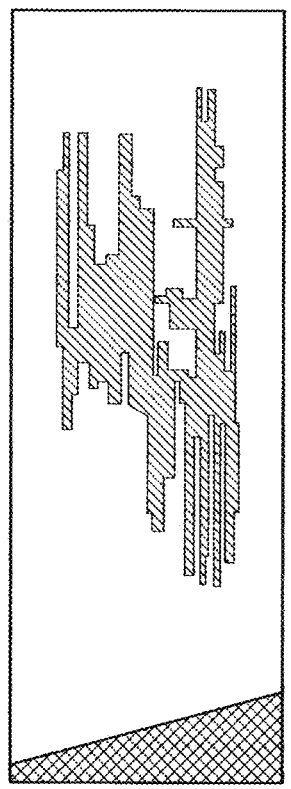
FIG. 14

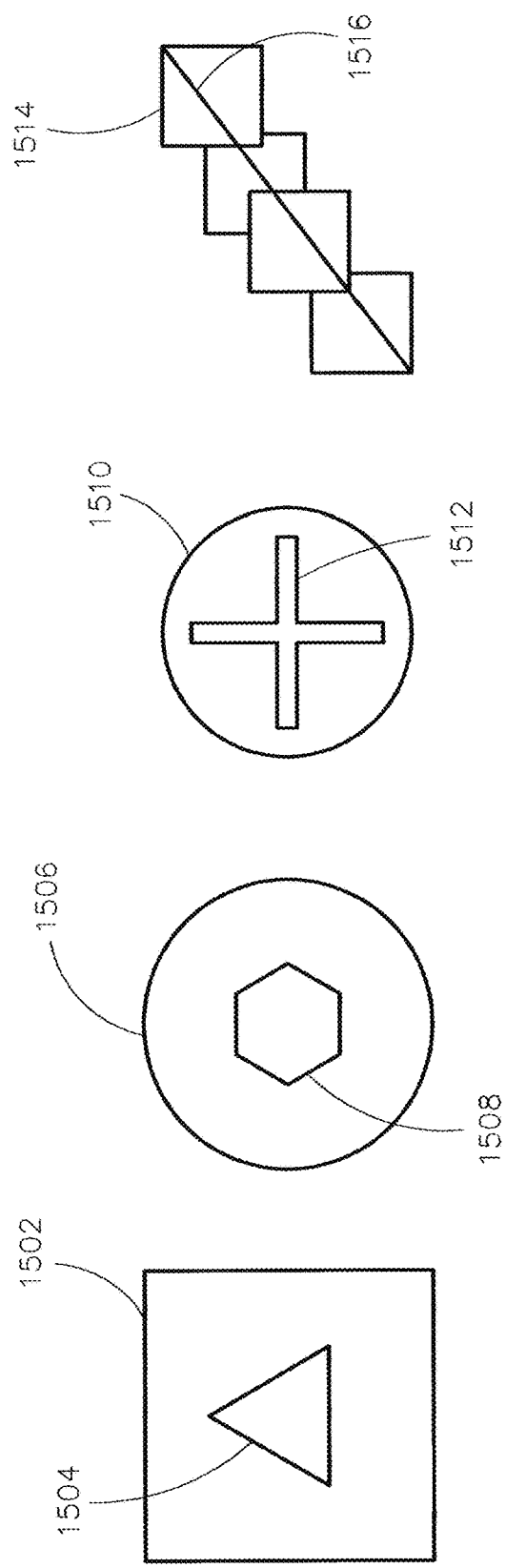

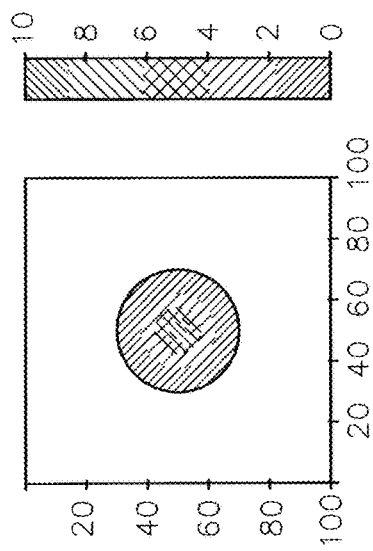
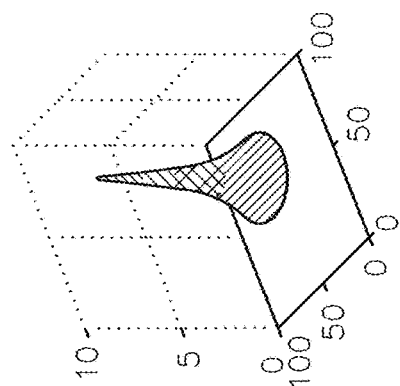
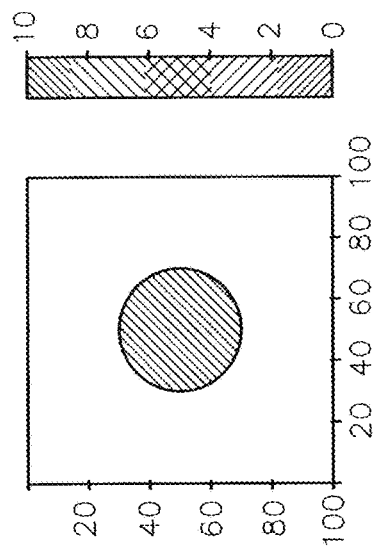
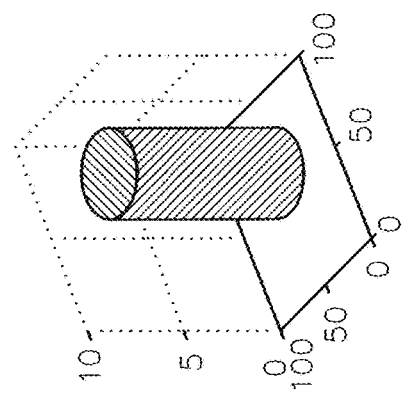
FIG. 19

US 10,330,608 B2

SYSTEMS AND METHODS FOR WAFER SURFACE FEATURE DETECTION, CLASSIFICATION AND QUANTIFICATION WITH WAFER GEOMETRY METROLOGY TOOLS

TECHNICAL FIELD

The disclosure generally relates to the field of wafer surface metrology, and particularly to systems and methods for wafer surface feature detection, classification and quantification with wafer geometry metrology tools.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Generally, certain requirements may be established for the flatness and thickness uniformity of the wafers. There exist a variety of techniques to address the measurement of shape and thickness variation of wafers. However, most existing wafer inspection tools can only inspect the wafer surface and detect the surface defects. Some wafer surface inspection tools may also calculate the defect areas and classify the defect types, but there is no information reported about the defect height or depth, and therefore there is no defect volume information provided by the existing inspection tools.

Therein lies a need for systems and methods for wafer surface feature detection, classification and quantification wherein the detected defects are classified and the important defect metrology information of height/depth, area and volume is reported, providing more values for quantifying the negative effect of these defects on the wafer quality.

SUMMARY

The present disclosure is directed to method for inspecting a wafer. The method may include setting up a data acquisition and a data processing recipe; acquiring a wafer surface image; filtering the wafer surface image to improve signal to background contrast; performing wafer edge treatment to suppress strong filter response; performing defect detection and classification based on the filtered wafer surface image; calculating at least one of: a height, a depth, an area and a volume of the defect utilizing surface fitting; and reporting the at least one of: a height, a depth, an area and a volume of the defect detected and classified.

A further embodiment of the present disclosure is directed to a method for inspecting patterned or filmed wafers. The method may include various data processing steps for a patterned wafer surface. Such steps may include correcting wafer XY distortions to obtain uniform patterns; generating a reference wafer and aligning the wafer under operation to the reference wafer; or performing wafer-to-wafer operations to suppress the pattern signal and produce residue wafer surface images. Similarly, the method may include various data processing steps for a filmed wafer surface. Such steps may include performing film response calibration and compensation for the filmed wafer surface to reduce signal variations from different film materials and film structures. Upon completion of such data processing steps, subsequent inspecting steps may include filtering the wafer surface image to improve signal to background contrast; performing defect detection and classification based on the filtered wafer surface image; calculating at least one of: a height, a depth, an area and a volume of the defect utilizing surface fitting; and reporting the at least one of: a height, a depth, an area and a volume of the defect detected and classified.

An additional embodiment of the present disclosure is directed to system for inspecting a wafer. The system may include an optical system configured for acquiring a wafer surface image. The system may also include a wafer surface feature detection, classification and quantification module. The wafer surface feature detection, classification and quantification module may be configured for: filtering the wafer surface image to improve signal to background contrast; performing defect detection and classification based on the filtered wafer surface image; calculating at least one of: a height, a depth, an area and a volume of the defect utilizing surface fitting; and reporting the at least one of: a height, a depth, an area and a volume of the defect detected and classified.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which:

FIG. 11 illustrates an example of slipline structure enhancement in accordance with the present disclosure;

FIG. 12 illustrates two exemplary non-linear shaped slipline defects;

FIG. 14 illustrates the detected slipline defects of FIG. 12;

FIG. 15 illustrates various types of image areas defined for performing surface fitting;

FIG. 19 illustrates the ability of the system and method in accordance with the present disclosure to provide volume information in addition to the defect height and area information.

DETAILED DESCRIPTION

Reference will now be made in detail to the subject matter disclosed, which is illustrated in the accompanying drawings.

Currently, certain wafer geometry metrology tools are capable of measuring the surface height of a wafer and providing nanotopography of the wafer. Nanotopography is defined as the deviation of a surface within a spatial wavelength of around 0.2 to 20 mm. Nanotopography bridges the gap between roughness and flatness in the topology map of wafer surface irregularities in spatial frequency. Since the flatness properties of incoming 200- and 300-mm wafers undergo only minor changes during wafer processing, precise and comprehensive measurement capabilities are necessary to detect minute variations in topography on the final wafer surface.

Wafer metrology tools and interferometer systems, such as WaferSight metrology system from KLA-Tencor, may scan both the front and back surfaces of a wafer at the same time. By combining wafer shape, edge roll-off, thickness or flatness, and nanotopography measurements in a single scan, such wafer metrology tools may provide complete data sets that are necessary for nanotopography and wafer geometry monitoring in wafer manufacturing.

The present disclosure is directed to systems and methods for providing micro defect inspection capabilities for optical systems such as wafer metrology tools and interferometer systems. The systems and methods in accordance with the present disclosure may detect, classify and quantify wafer surface features, wherein the detected defects are classified and the important defect metrology information of height/depth, area and volume is reported. The systems and methods in accordance with the present disclosure therefore provide more values for quantifying the negative effect of these defects on the wafer quality.

Figure 1:
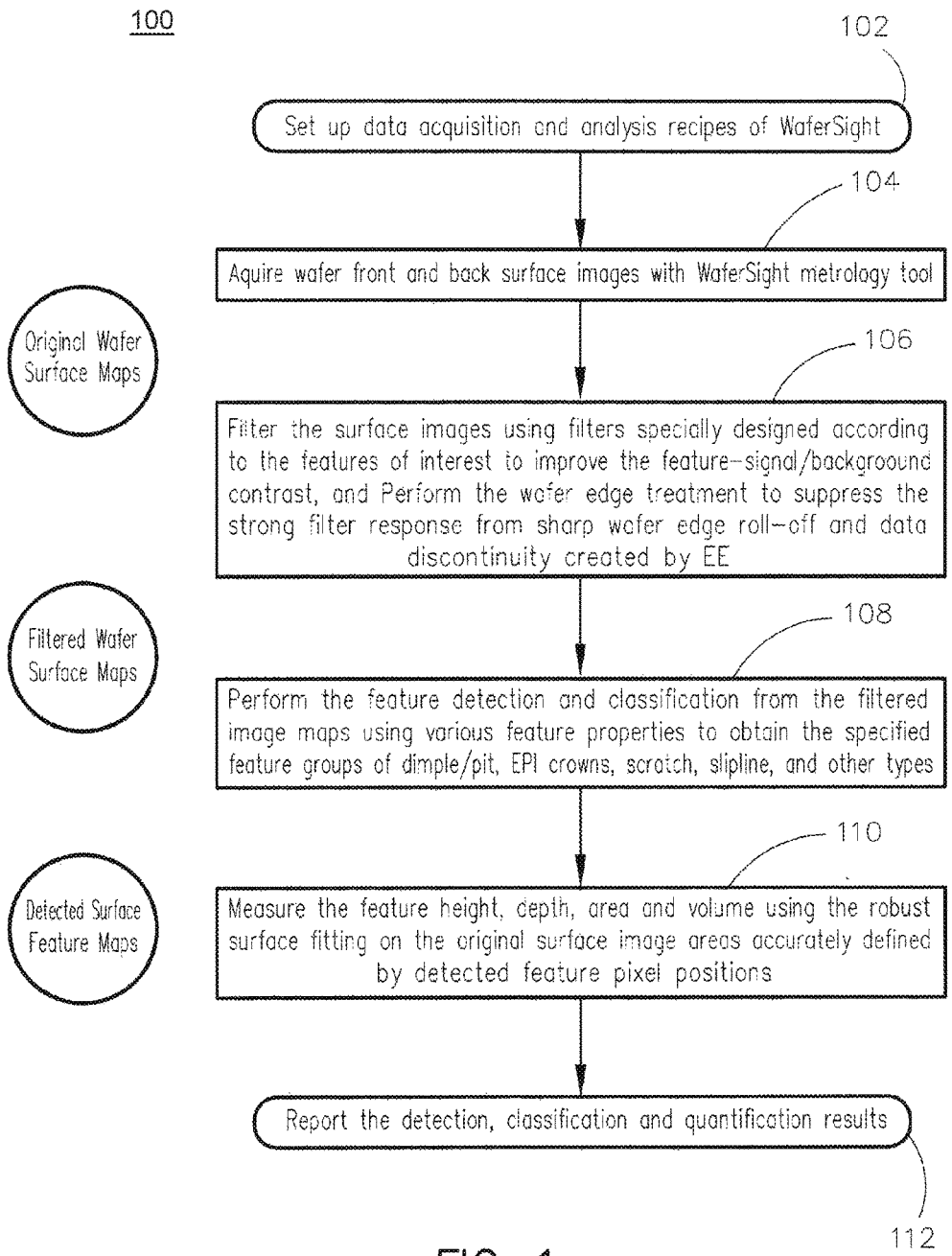
FIG. 1 is a flow diagram illustrating a method for detection, classification and quantification of bare wafer surface defects.

FIG. 1 shows a flow diagram illustrating major steps performed by a method 100 for detection, classification and quantification of bare wafer surface defects in accordance to the present disclosure. In step 102, the data acquisition and the data processing recipe is set up. In step 104, the wafer surface images (e.g., the front and back surface images) are acquired using an optical system such as WaferSight. In step 106, the surface images are filtered using specially designed filters according to the features of interest to improve the feature signal to background contrast, and the wafer edge treatment is performed to suppress the strong filter response from the sharp wafer edge roll-off or from the data discontinuity created by the wafer edge exclusion.

Various types of filters may be utilized in step 106. For instance, filters such as a double Gaussian high-pass filter, a Laplace band-pass filter, a Sobel line filter or the like may be applied on the surface image maps acquired in step 104. These filters may remove the long wavelength shape components in the original wafer surface images and thus boost the defect feature signal to the background contrast of the wafer surface images. However, these filters may have strong response in the wafer edge region due to the sharp wafer edge roll-off or the data discontinuity created by the wafer edge exclusion operation. The strong edge response may affect the detection capability of defect features in the wafer edge region, such as edge EPI crowns and sliplines.

Figure 3:
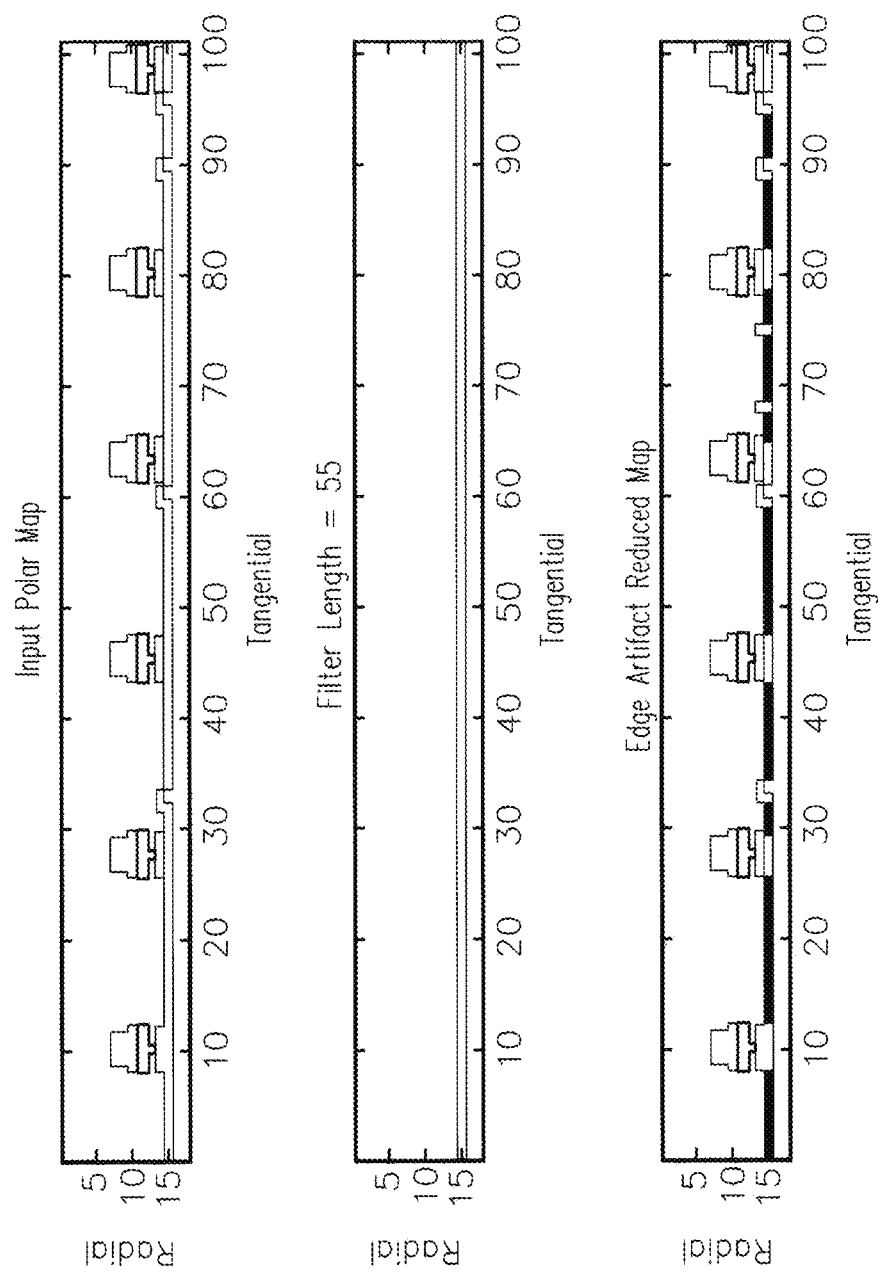
FIG. 3 illustrates exemplary mapping images for a wafer edge treatment process.

To suppress the strong filter response from the wafer edge region or from the data discontinuity created by the edge exclusion, the following edge treatment operations may be performed:

a) Convert the wafer edge region into an image band in polar space. The band height direction is the radial direction and the size in this direction is determined by the filter kernel size and the wafer roll-off profile sharpness. The band width direction is the tangential direction and the size in this direction is determined by the sampling rate in the angular direction.

b) Perform the one-dimensional median filtering on this band image along the tangential direction row by row. The filter length is selected to be able to follow the trend of the edge profile variations in the angular direction and preserve the interested edge feature in the edge treatment. Currently, the filter length is defaulted to cover a five-degree data span. It can be adjusted according to the feature angular property for the optimal performance.

c) The filtered image is subtracted from the original image to obtain the edge response suppressed image. One segment of the original edge image, the filtered edge image and the edge artifact reduced image are shown in FIG. 3 for illustrative purposes.

d) Since the edge region usually has more noisy signals than the wafer interior region, to reduce the noise components in the edge region while preserving the feature signal, the following polarity trimmed mean may be performed on the edge-treated image in the very edge region, where invalid pixels will exist due to the measurement capability limit of the metrology system. That is, for the given pixel $I(x,y)$ from the median filter edge treatment in step c), the trimmed output signal $O(x,y)$ will be calculated as defined in:

$$O_+(x, y) = \frac{1}{N_+} \sum_{(dx,dy) \in A_+} I(x+dx, y+dy), \text{ when } I(x, y) > 0$$

$$O_-(x, y) = \frac{1}{N_-} \sum_{(dx,dy) \in A_-} I(x+dx, y+dy), \text{ when } I(x, y) < 0$$

Where, $A_+$ and $A_-$ are the positive and negative pixel sets inside the filter window, $N_+$ and $N_-$ are the numbers of the positive and negative pixels, respectively. In other words, if $I(x,y)>0$, then take the average of the positive pixels in the specified filter window; otherwise, if $I(x,y)<0$, take the average of the negative pixels in the specified filter window.

It is contemplated that this polarity trimmed mean will effectively reduce the edge noise components and preserve the signal contrast of many bipolar defect signals from EPI crowns and sliplines. This helps to obtain the improved performance for defect detection and classification in the wafer edge regions. It is also contemplated, however, that the various types of filters and the filter response suppression techniques described above are exemplary. Other types of filters and noise reduction techniques may also be utilized in step 106 without departing from the spirit and scope of the present disclosure.

Subsequently, the defect detection and classification steps in accordance with the present disclosure may be performed to produce defect maps, composed of various defect groups and defect positions. Useful defect properties may be calculated according to these defect types and the defect positions, and may then be used to define the positions, size and shape of the measurement areas on the wafer surfaces. From these measurement areas, the accurate defect height/depth, area and volume may be calculated and reported to provide valuable information for wafer production.

For instance, step 108 may perform the feature detection and classification from the filtered image maps using various feature properties to obtain the specified feature groups of interest, such as dimples/pits, wafer edge EPI crowns, scratches, sliplines and the like. The term dimple/pit may refer to a surface depression; edge EPI crowns may refer to the difference between the surface elevation from the edge of the slice (associated with epi layer deposition); scratch may refer to a shallow groove or cut below the established plane of the surface; and slipline may refer to a process of plastic deformation in which one part of a crystal undergoes a shear displacement relative to another in a manner that preserves the crystallinity of each part of the material. Step 110 may measure the feature height, depth, area and volume using the robust surface fitting on the original surface image areas accurately defined by detected feature pixel positions, and the detection, classification and quantification results may be reported in step 112.

Figure 2:
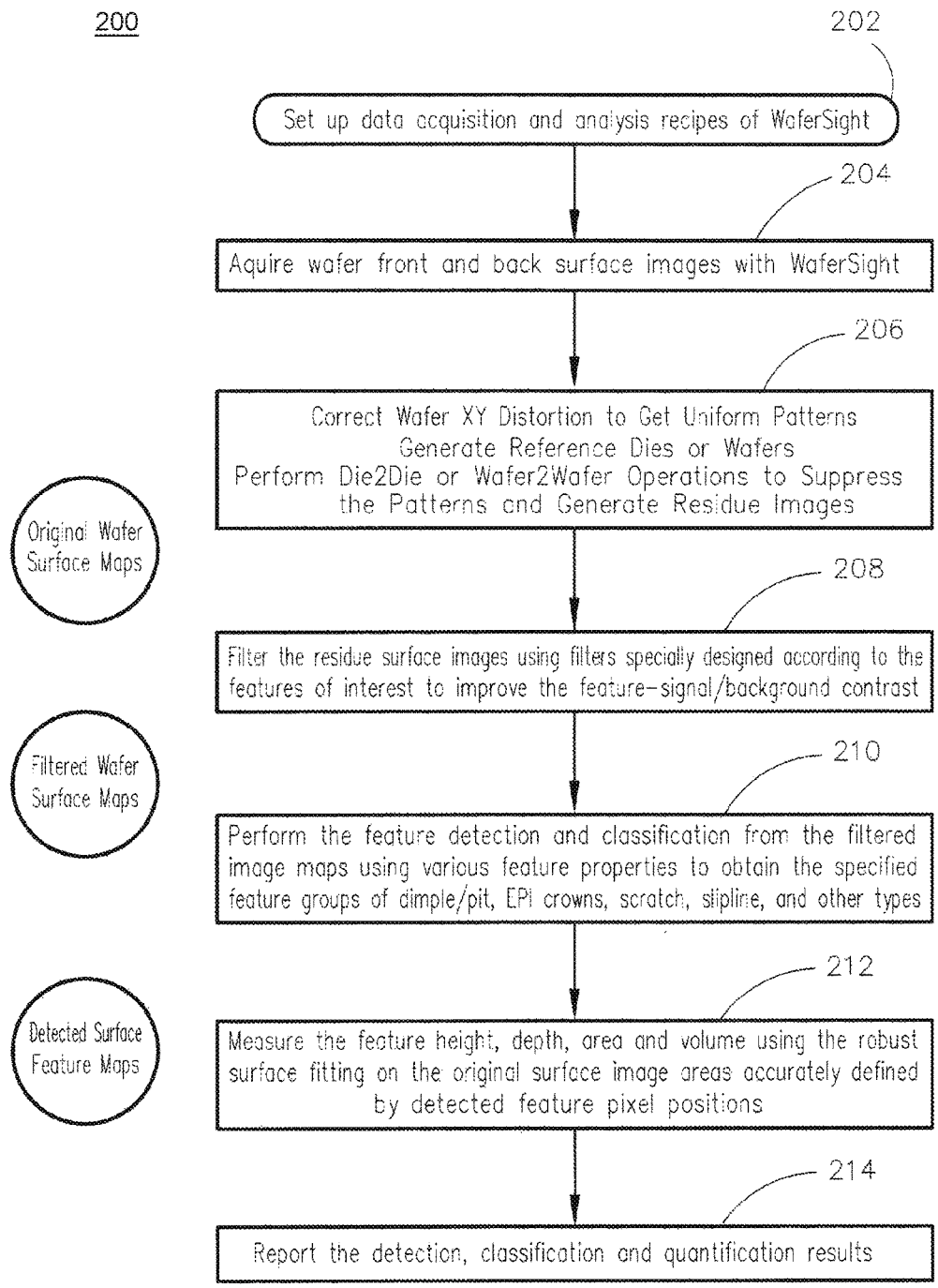
FIG. 2 is a flow diagram illustrating a method for detection, classification and quantification of patterned wafer surface defects.

It is contemplated that while method 100 may be applied to bare wafer surface defects detection, classification and quantification, patterned wafer surface defects may need to be handled differently. FIG. 2 shows a flow diagram illustrating major steps performed by a method 200 for detection, classification and quantification of patterned wafer surface defects in accordance to the present disclosure. Similar to steps 102 and 104 described above, steps 202 and 204 may set up the data acquisition and the data processing recipe of the optical system (e.g., WaferSight) and acquire the front and back surface image data of the wafer. After that, however, many steps of the data processing common in the patterned wafer inspection may be performed in step 206.

Some operations performed in step 206 for the patterned wafer applications may include, for example: correcting the wafer XY distortions according to the calibrated system XY pattern so that the wafer surface image will have uniform patterns; generating the reference die and/or reference wafers from the neighboring dies or previously acquired wafer image data; aligning the die under operation to the reference die or align the wafer under operation to the reference wafer; and/or performing the die-to-die or wafer-to-wafer operations to suppress the pattern signal and produce the residue wafer surface images. It is contemplated that such operations specially required for the patterned wafer may be carried out only on the front wafer surface where the films and chip patterns are manufactured on. For the back wafer surface, most of the method steps for the bare wafer may be utilized directly or with some small modifications to cover the special properties introduced by the patterning on the front wafer surface.

After the residue wafer surface images are generated, the similar data processing procedures described in the system and methods for bare wafer inspection may be utilized. That is, step 208 may filter the residue surface images using specially designed filters according to the features of interest to improve the feature signal to background contrast. Step 210 may perform the feature detection and classification from the filtered image maps using various feature properties to obtain the specified feature groups of interest, such as dimple/pit, wafer edge EPI crowns, scratch, slipline and the like. Step 212 may measure the feature height, depth, area and volume using the robust surface fitting on the original surface image areas accurately defined by detected feature pixel positions, and the detection, classification and quantification results may be reported in step 214.

Steps 108 and 110 (and steps 210 and 212) may be jointly referred to as the detection, classification and quantification steps. They will now be described in detail for various features of interest, such as detection and classification of wafer edge EPI crowns, detection and classification of scratches, detection and classification of slipline, as well as defect quantification by adaptive robust surface fitting.

Figure 4:
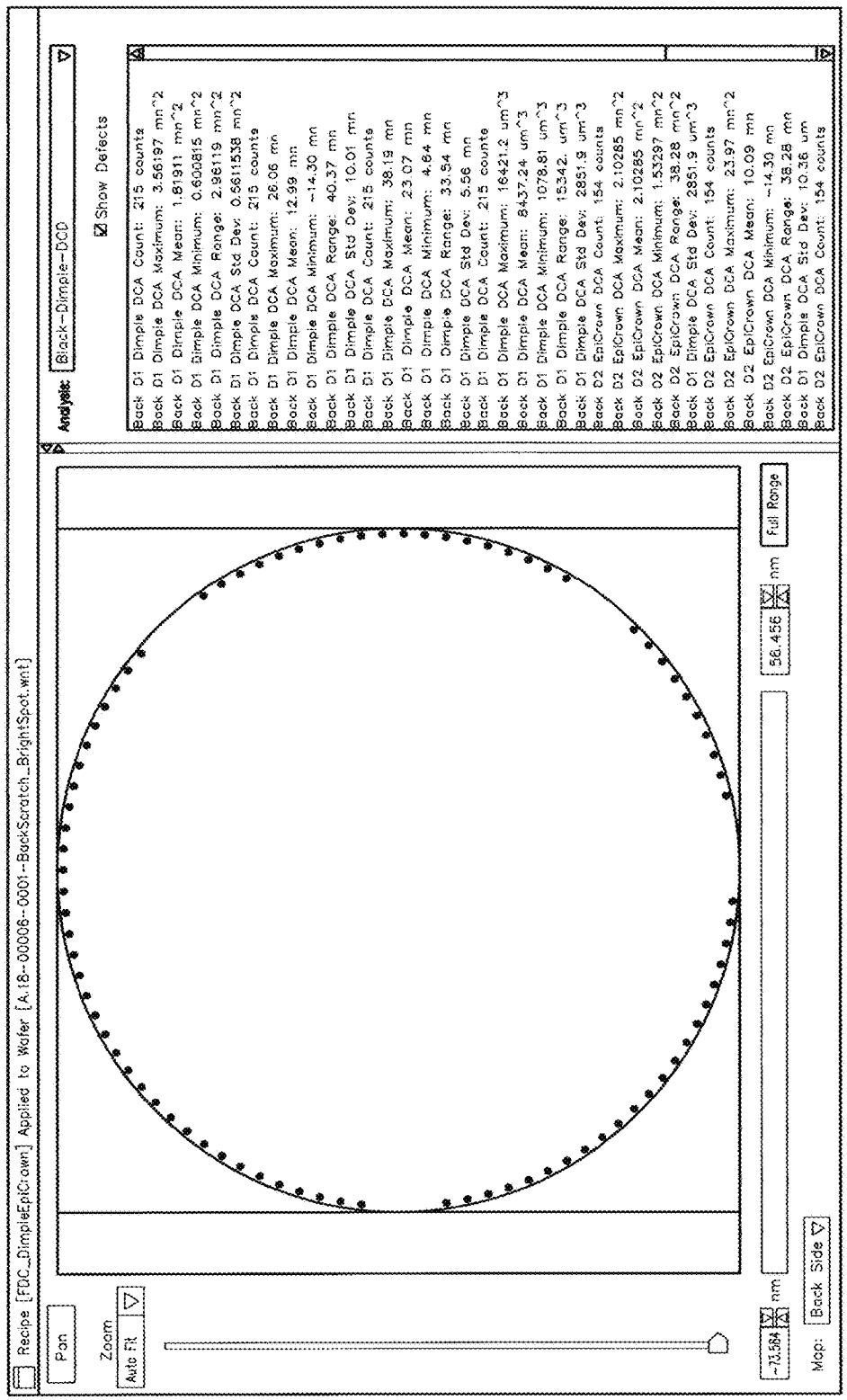
FIG. 4 illustrates an exemplary image containing detected EPI crowns.

In one embodiment, step 108 (and step 210) may be configured for detection and classification of wafer edge EPI crowns. Wafer edge EPI crowns are defined as periodic bumps or dimples that occur in a circular pattern with a specific spatial frequency. These EPI crowns are typically located at a fixed distance from the wafer edge. A surface image of the wafer obtained using a metrology tool may be processed (e.g., as described in step 106 for a bare wafer or steps 206 and 208 for a patterned wafer) to detect such wafer edge EPI crowns and the statistics of their metric values. FIG. 4 depicts an exemplary image containing the detected EPI crowns.

Figure 5:
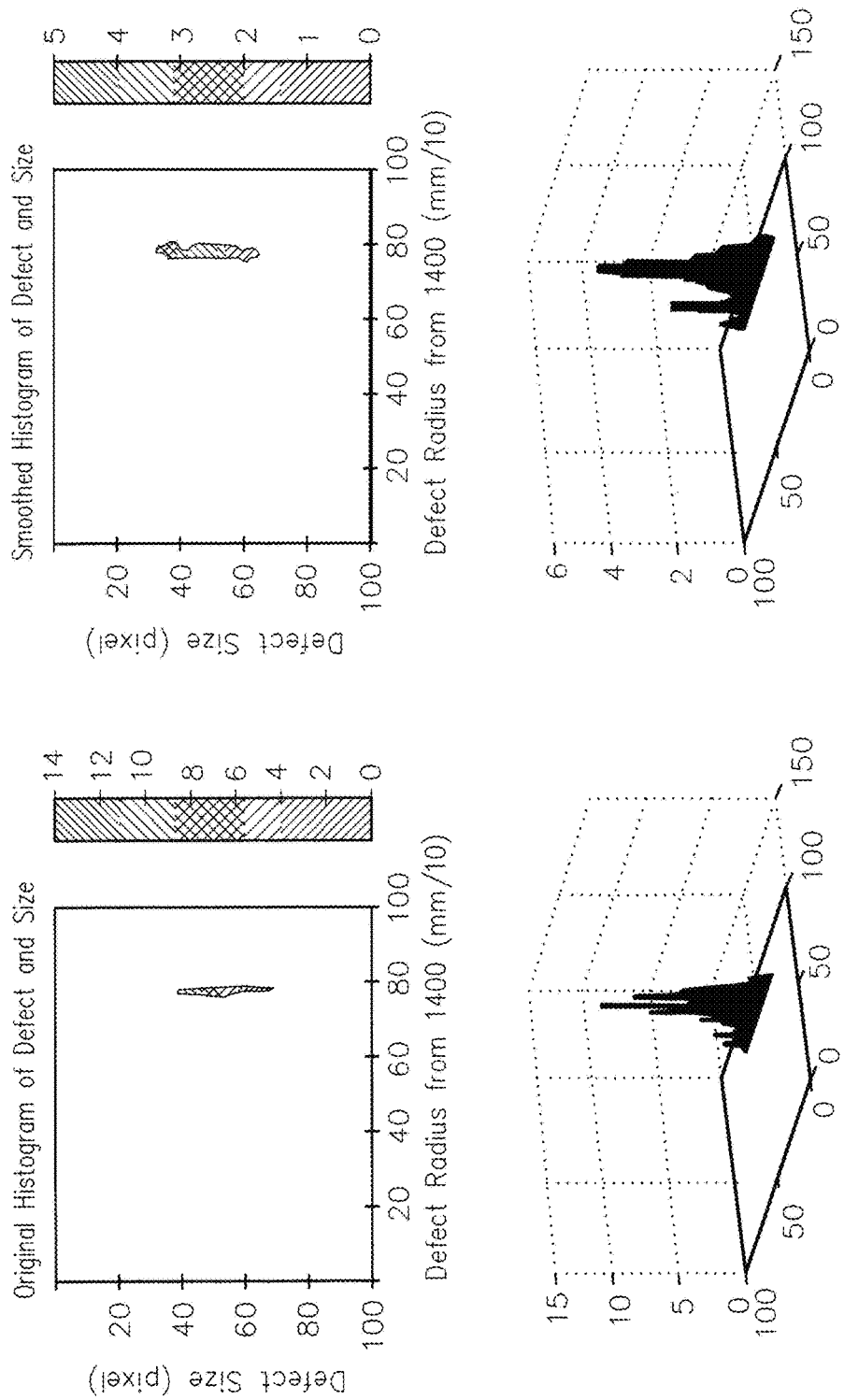
FIG. 5 illustrates two-dimensional radius-size histograms generated based on the radius positions and the sizes in pixels of the detected EPI crowns.

The locations and the metric values of the detected EPI crowns may be utilized for reliable detection and classification of defects. For instance, the detection and classification process may first form a two-dimensional radius-size histogram (shown in FIG. 5) based on the radius positions and the sizes in pixels of the detected EPI crowns. The detection and classification process may then smooth the histogram utilizing any histogram smoothing technique, and the peak position of the smoothed histogram may indicate the estimated EPI crown radius position and their most plausible size. For the exemplary image of FIG. 4, the estimated radius of these EPI crowns is 147.9 mm and the estimated defect size is 45 pixels for one particular image resolution setting.

Figure 6:
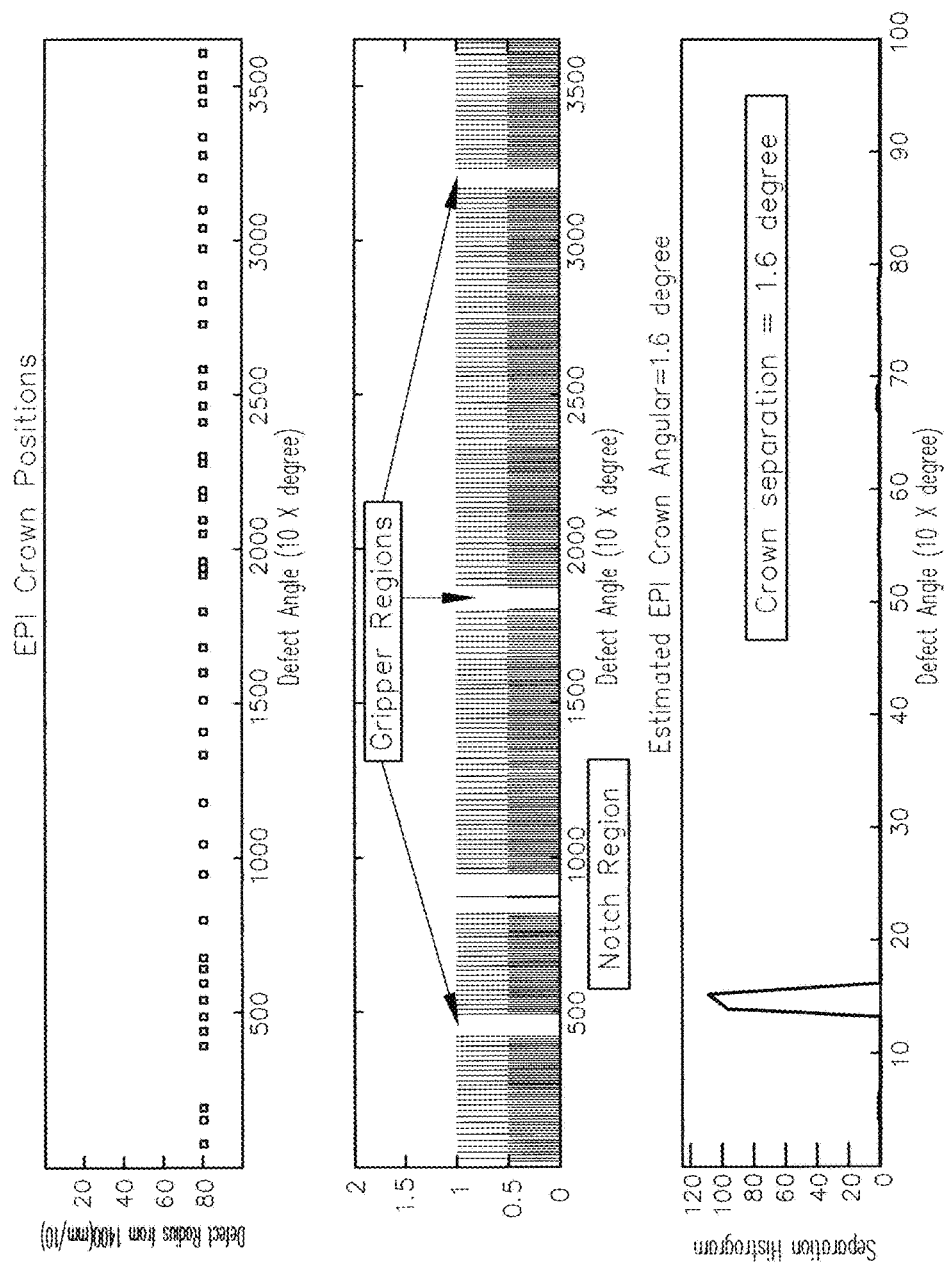
FIG. 6 illustrates projections of the angular positions of the defect pixels in the wafer edge region.

The detection and classification process may then estimate the angular separation of the EPI crowns. In one embodiment, as shown in FIG. 6, the angular positions of the defect pixels in the wafer edge region are projected onto the angular axis and the histogram of the angular separations between the neighboring defects is calculated. As shown in FIG. 6, although there are missing data segments from three wafer gripper regions and the wafer notch region in the signal projection (such regions are indicated in FIG. 4 as well), this process can still produce a very good estimate for the angular separation of these EPI crown defects. In this particular example, the estimated angular separation between the EPI crowns is 1.6 degree.

Subsequently, the detection and classification process may utilize the estimated defect radius R, defect size S and defect separation T in the classification to sift the candidate defects. For instance, if the radius, size and separation values of the defects have bigger distances from these estimated reference values than three specified thresholds for them, they will not be considered as EPI crowns. Since the estimated angular separation provides the period information about the EPI crown signal, it can also be used to enhance the EPI crown signal in the frequency domain for improved performance.

Figure 7:
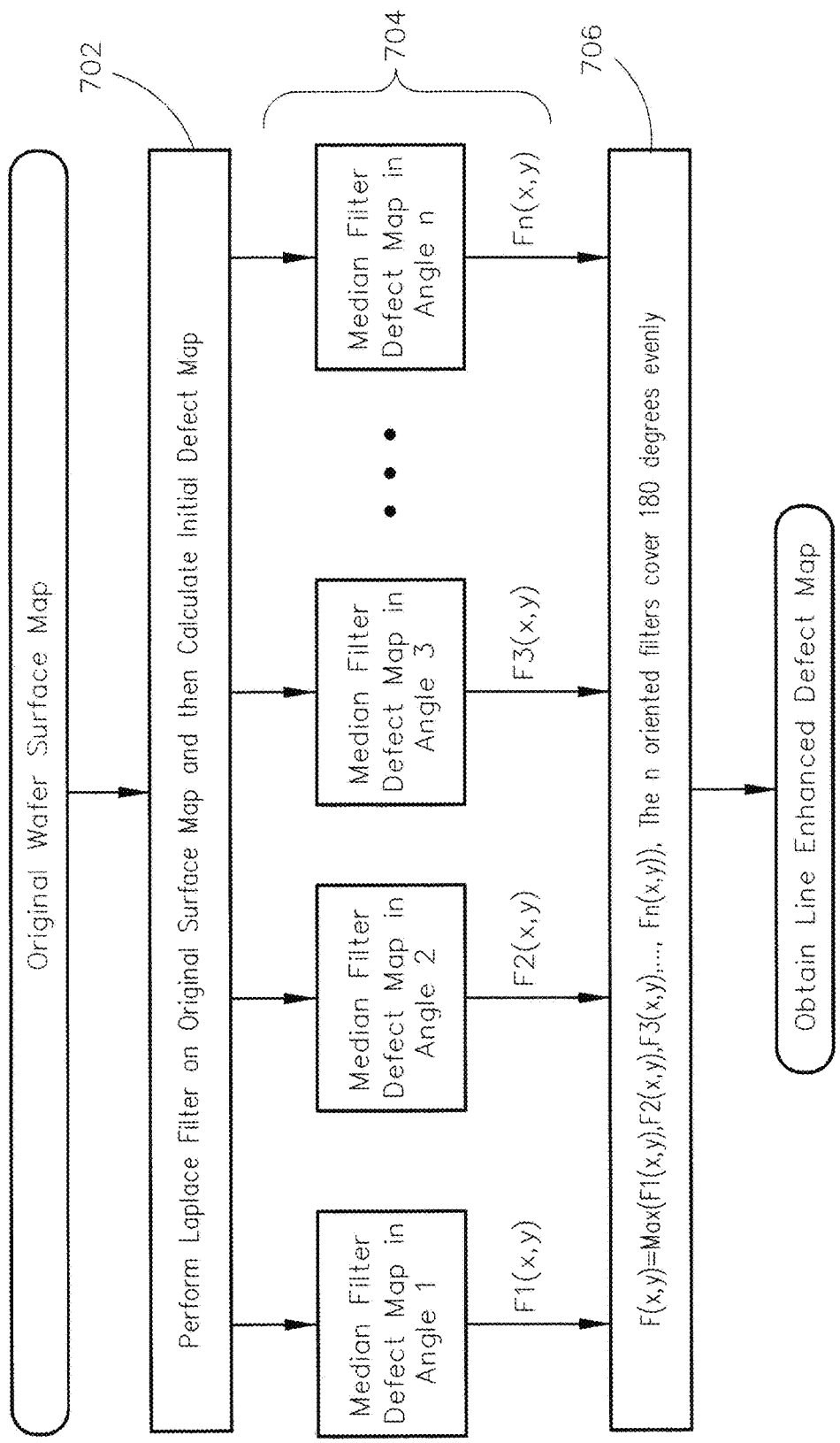
FIG. 7 is a flow diagram illustrating a method for scratch detection and classification process.

In addition to detection and classification of wafer edge EPI crowns, step 108 (and step 210) may also be configured for detection and classification of scratches. As illustrated in the flow diagram in FIG. 7, the major processing steps of the scratch detection and classification process are shown. In one embodiment, upon receiving the acquired wafer surface images, step 702 may perform Laplace filtering on the wafer surface images to remove the low frequency surface shape components. Subsequently, a simple intensity threshold or a background adaptive threshold map is used to obtain the initial defect map represented in binary format. For many faint surface scratches with depth less than 2 nm, the scratch signal from the metrology tool may often appear as broken points along the scratch and cannot be reliably separated from other surface features with small extents, making the accurate detection and classification of scratch very difficult. Utilizing this line enhancement technique in accordance with the present disclosure, these broken scratch data points can be effectively connected and other small feature structures can be removed.

In one embodiment, step 704 may process the input defect map using the filter bank in parallel. First, the input defect map is rotated about the wafer center with different angles which equally span the 180 degrees. Then the one dimensional median filtering is performed on the rotated image in the image row direction and the data processing is carried for each image out row by row. In this manner, the neighboring data required in the filtering will be in the cache and the fast processing speed can be achieved. Subsequently, the outputs of these oriented filters will be selected using the maximum rule for each pixel position in step 706. All these operations may be implemented using the Intel Integrated Performance Primitive (IPP) library and the data processing may be performed on the binary image, not on the integer or float type images of the original surface images or the filtered surface images. As a result, the scratch signal enhancement process in accordance with the present disclosure can achieve good scratch enhancement and throughput performance.

Figure 8B:
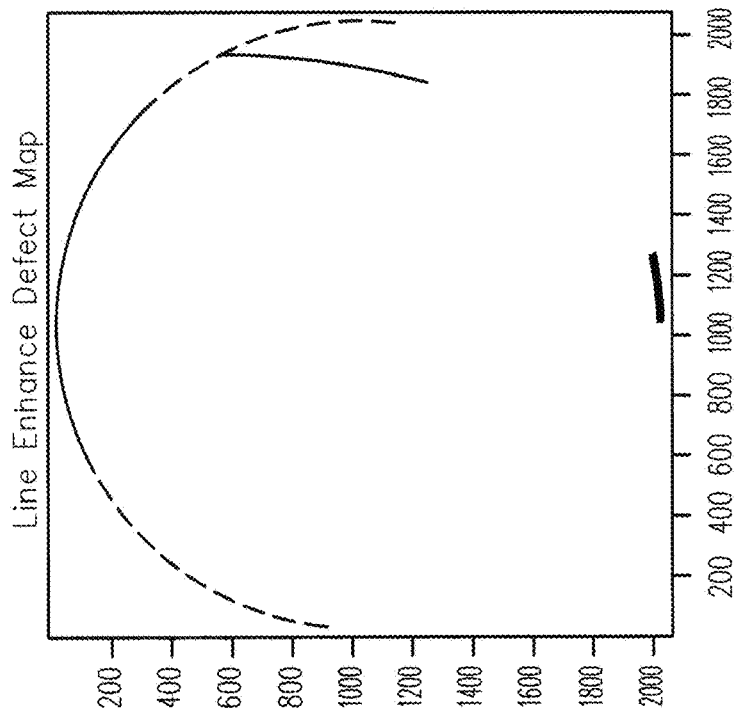
FIGS. 8 and 9 illustrate an example of scratch structure enhancement in accordance with the present disclosure.
Figure 8A:
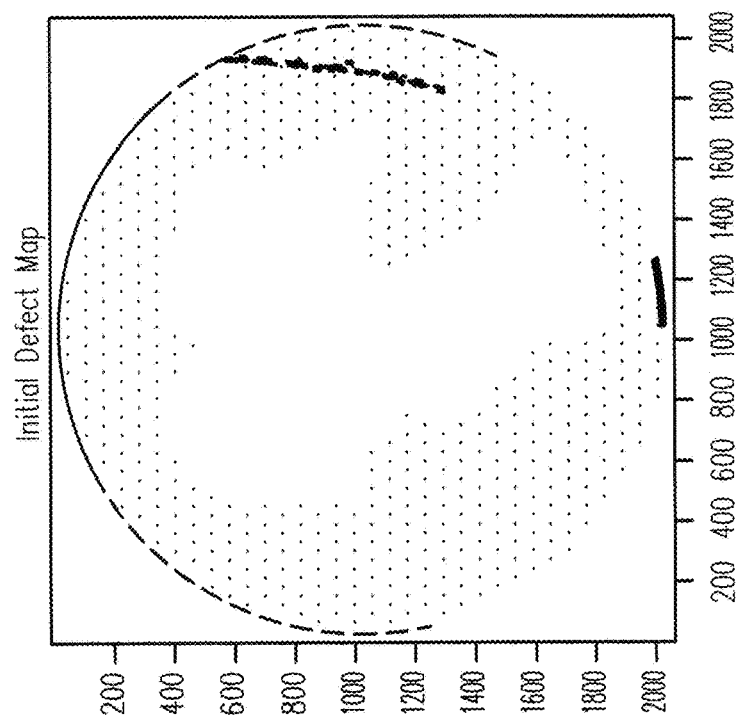
Figure 9A:
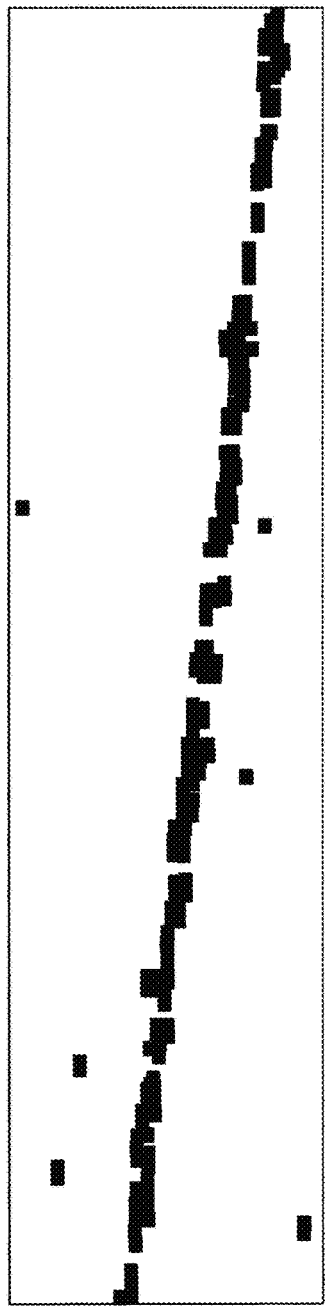
Figure 9B:
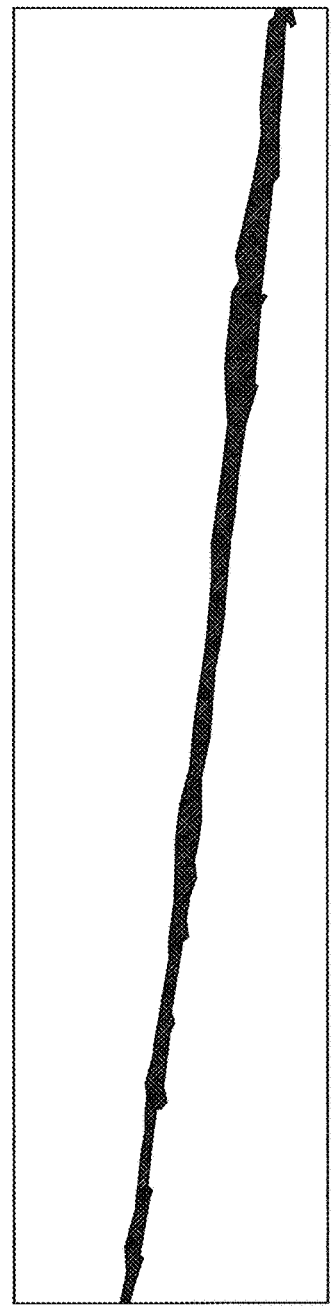

Coming out from this scratch enhancement process, all gaps shorter than the half of median filter length along the scratch will be bridged and all other features shorter than half of median filter length will be removed. One example of the scratch structure enhancement is shown in FIG. 8, where FIG. 8A is the initial defect map obtained and there are many broken segments from the scratch and other isolated defects. FIG. 8B shows the enhanced defect map. The zoomed-in scratch part is shown in FIG. 9. It is clear that the broken scratch segments are well connected and the isolated defect points are effectively removed. Therefore, the scratch enhancement process effectively improves the reliability and accuracy for detection, classification and quantification of scratches.

Furthermore, step 108 (and step 210) may also be configured for detection and classification of sliplines. Sliplines are structural flaws that occur along the crystallographic planes of the silicon lattice. Such features may be common in two distinct regions: near the edge of the wafer and in the location where process chamber pins support the wafer. The techniques for effective slipline detection and classification in accordance with the present disclosure are designed to improve the feature definition and minimize the damage to the slipline signal by enhancing the line structures differently in the different wafer regions to cover two slipline use cases.

It has been observed that the slipline orientation depends on the wafer crystal orientation and the edge slipline orientation strongly depends on the sectors where the crystal structure strength is weaker. Wafer manufactures use the wafer notch and flat to indicate the wafer crystal structure orientation, and the method for detection and classification of sliplines may utilize such wafer properties to define the different line enhancement regions.

Figure 10:
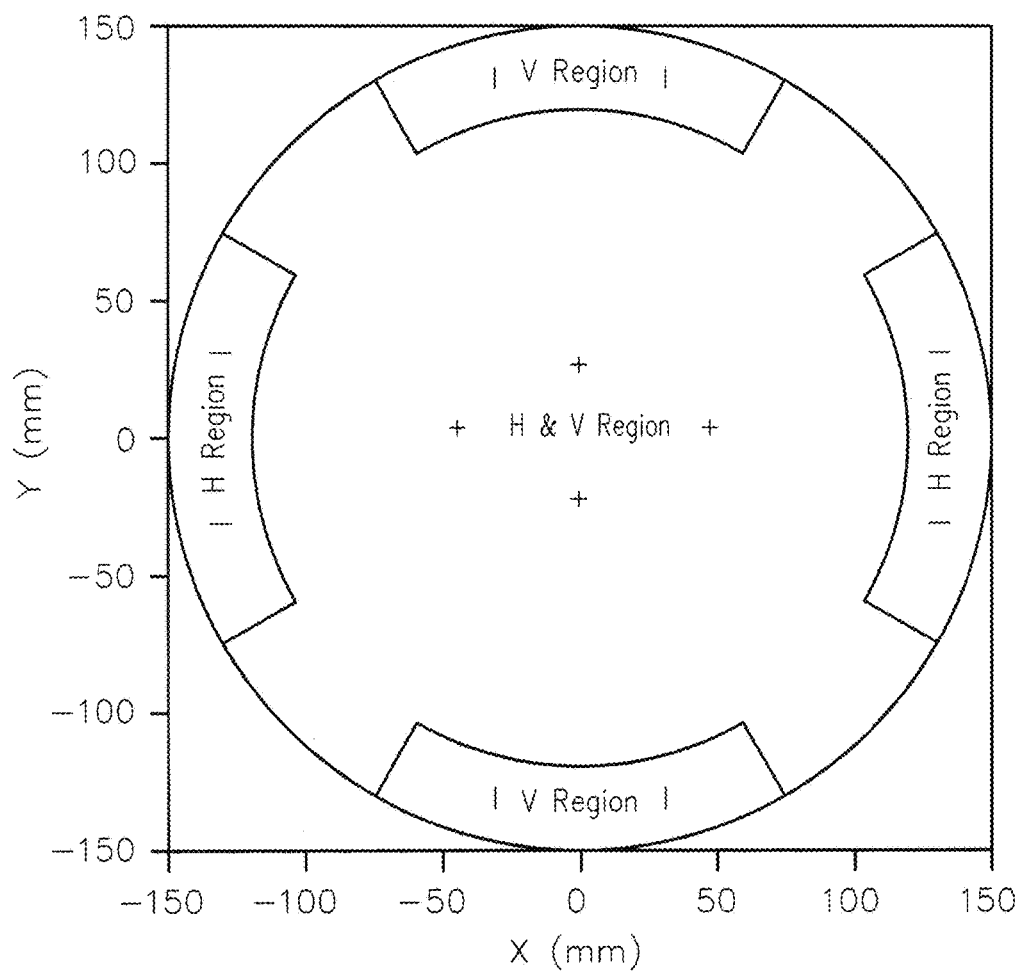
FIG. 10 illustrates partitioning a wafer surface for slipline structure enhancement.

For instance, the slipline detection and classification process may partition the wafer surface to different regions for the slipline structure enhancement, as shown in FIG. 10. More specifically, FIG. 10 depicts an exemplary 300 mm wafer and the wafer surface crystal orientation is indicated in a pattern described by the Burgers vector. The slipline detection and classification process may perform the line enhancement techniques described above in FIG. 7 for each region. For instance, in the V regions, the line enhancement using the one-dimensional median filter may be carried out only in vertical direction, and in the H regions, the line enhancement using the one-dimensional median filter may be carried out only in horizontal direction. In the H&V region, both vertical and horizontal enhancement filtering may be performed, which is a special case of the line enhancement described above in FIG. 7. With this data processing plan, the edge sliplines are smoothed and connected without introducing the crossing between them, which will damage the resolution of these short edge sliplines.

One example of the slipline enhancement by the process described above is shown in FIG. 11. The differences between the original slipline defect map (left) and the processed slipline defect map (right) demonstrate the effectiveness of line enhancement and noise removal.

It is contemplated that, in addition to the enhancement process described above, more complex partition and weighting transition schemes may be used for improved performance at the cost of more required computation. For the wafers with other crystal orientations, the same principles may be utilized to partition the wafer surface into different regions and apply the line filters in different orientation in these regions for the most effective slipline enhancement.

It is also contemplated that in the acquired wafer images, the sliplines may have different shapes from the ideal line shapes as shown in the left side image of FIG. 12. In this example, the slipline structures are connected to span a large region. Furthermore, in some other cases, several sliplines are merged together to form one defect object and do not resemble a line shaped object anymore as shown in the right side image of FIG. 12. The cases like these make the accurate classification of sliplines very difficult when only using the standard line definitions, such as the length/width ratio of the bounding box.

Therefore, to more effectively handle the complicated slipline cases, a new method for identifying slipline features is proposed. This new method extends from the histogram of oriented gradients (HOG) used for image recognition, where the image is partitioned into the areas of a regular rectangular grid and then the histogram of the oriented gradients of each image region is calculated to form a feature vector.

When applied to slipline detection and classification, instead of calculating HOG for the regular image areas, the HOG of each binary defect object is calculated. This method may therefore be referred to as OHOG for Object Histogram of Oriented Gradient. Different from the conventional image HOG, where all pixels in the image region make the contribution to the calculated HOG, OHOG gets the contributions only from the boundary pixels of the defect objects, since the interior pixels of the binary defect areas have zero difference. Therefore, the new method has high sensitivity to the shape and orientation of the defect objects and can be used to help identify the slipline defects.

Figure 13:
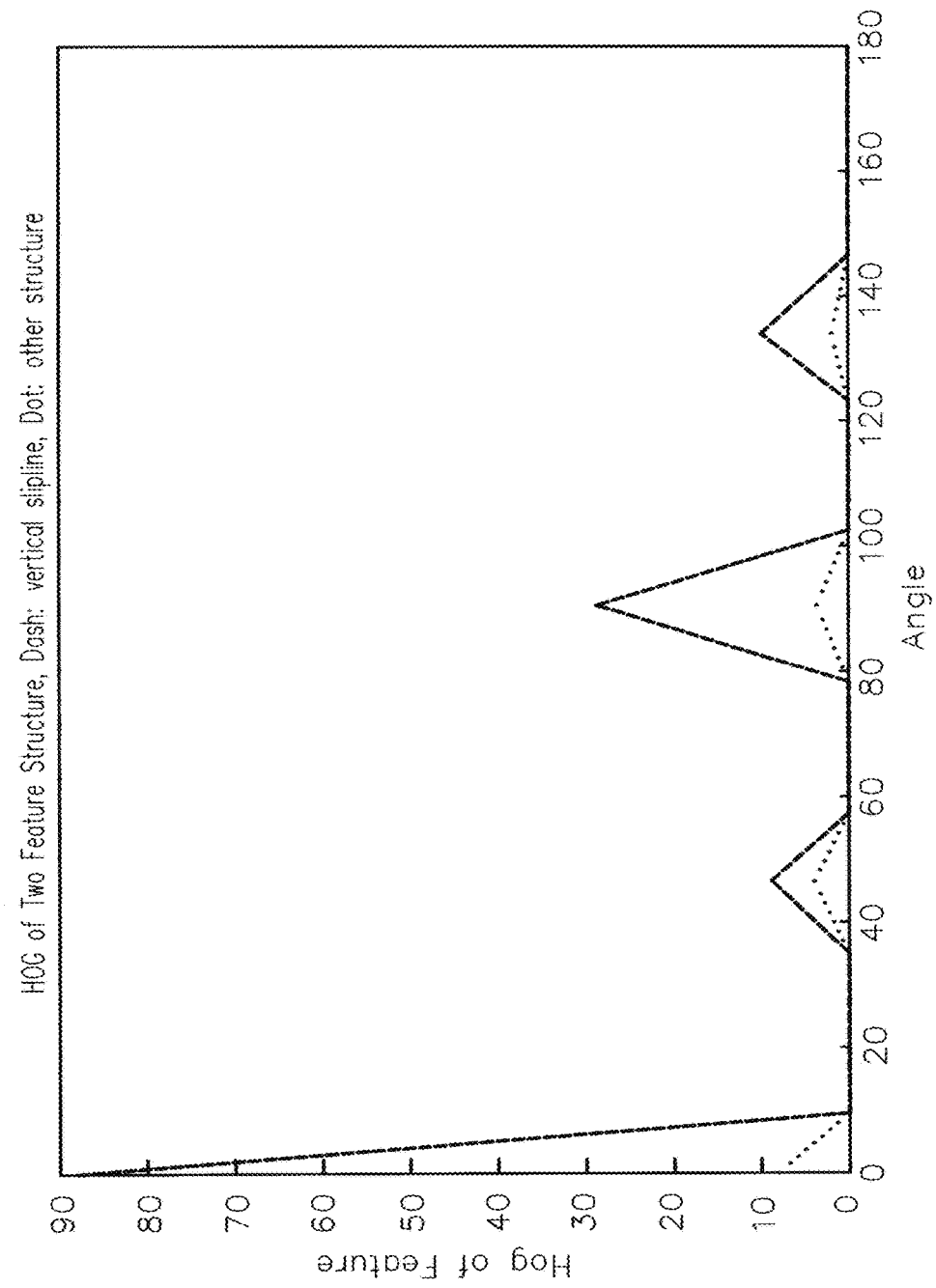
FIG. 13 illustrates two object histogram of oriented gradient plots for two defect objects.

FIG. 13 illustrates two OHOG plots for two defect objects. The solid lines are for a vertical slipline and the dashed lines are for a non-slipline defect. In this example, sixteen bins of angles have been used to provide enough feature angular resolution in the OHOG. It can be seen that the vertical slipline has a much stronger histogram peak at 0 degree gradient orientation, while other defect object has very similar peak distributions in different orientations. This information is very important to obtain the correct classification for the cases similar to the slipline defect structures as shown in FIG. 12. Utilizing OHOG in accordance with the present disclosure allows the two exemplary slipline defects of FIG. 12 to be detected and classified correctly, as indicated in FIG. 14.

In addition to detection and classification of wafer defects, bumps, dimples, EPI crowns, scratches and sliplines as described above, method 100 and 200 in accordance with the present disclosure may also be utilized for the reliable detection and classification of many other types of surface defects, which have the measurement values deviated from the local image surface and have enough defect feature signal to background noise ratio. These defects may have different shapes and polarities, and may be located anywhere on the wafer surface. For patterned wafers, the defect and background signals are defined on the image map after pattern removal by techniques such wafer-to-wafer or die-to-die image subtraction. In such cases, in addition to the defects described above, many pattern defects such as missing or extra pattern structures can also be detected and classified.

It is contemplated that the method 100 and 200 in accordance with the present disclosure may also be utilized for detect quantification by adaptive robust surface fitting. That is, in addition to detecting the defect area, accurate information regarding defect height/depth and defect volume can also be calculated in step 110 (and step 212) using the adaptive robust surface fitting method. The ability to calculate accurate height/depth and defect volume information utilizing the method in accordance with the present disclosure provides much more useful defect information for the process control in wafer and chip manufacturing compared to conventional detection methods.

Since the defects on the wafer surface have been identified in the detection stage (i.e., in step 108 or 210, respectively), many useful defect geometry properties can be calculated from their positions, such as the mass center $O(x_0,y_0)$, the maximum distance $R_{d,max}$ of the defect pixels to its mass center, percentage of the defect area to the minimum bounding box area and the like. Such defect geometry properties may then be used to define the position, shape and size of the image area in the original surface image maps for accurate defect quantification.

For example, from the defect mass center $O(x_0,y_0)$ and the maximum center-to-boundary distance $R_{d,max}$, a rectangular image area can be defined to center at $O(x_0,y_0)$ and with the area side length $L=K \times R_{d,max}$, where $K(>2)$ is an area scaling constant so that the defect will be fully contained inside of this rectangular image area and there are enough non-defect image pixels for the estimate of the reference surface. FIG. 15A depicts an exemplary rectangular image area 1502 that contains defect 1504. In addition to rectangular image areas, disk shaped image areas may also be used. In this case, the disk center is aligned with the defect mass center $O(x_0,y_0)$ and the disk radius is larger than $2 \times R_{d,max}$. FIGS. 15B and 15C depict such disk shaped image areas 1506 and 1510 for containing defects 1508 and 1512, respectively.

It is contemplated that the rectangular and disk shaped image areas described above are exemplary. Image areas of various different shapes may also be utilized without departing from the spirit and scope of the present disclosure. Furthermore, if the defect shape is not very solid, whose area is a small percentage of the area defined by the minimum bounding box, then a tighter image area may be used since enough non-defect image pixels can still provide a good estimate for the reference surface. It is also contemplated that for a long extent defect, such as a long scratch 1516 as illustrated in FIG. 15D, the measurement may be carried out in a scanning mode, with a measurement window 1514 moving along the scratch trace automatically guided by the defect pixel positions.

After the image area is defined, the surface fitting with proper polynomial orders, which are determined by the defect type and the area for the surface fitting, is performed on this image area of the original surface image with the pixels in the detected defect positions excluded in the fitting process. Then the estimated defect surface profile $D(x,y)$, i.e., the shape corrected surface image, can be calculated from the original surface image $I(x,y)$ and the fitted surface image $F(x,y)$ according to the equation: $D(x,y)=I(x,y)-F(x,y)$. Subsequently, the defect maximum height value and the maximum depth value can be found from the pixel values of $D(x,y)$ on the detected defect pixel positions.

Figure 16:
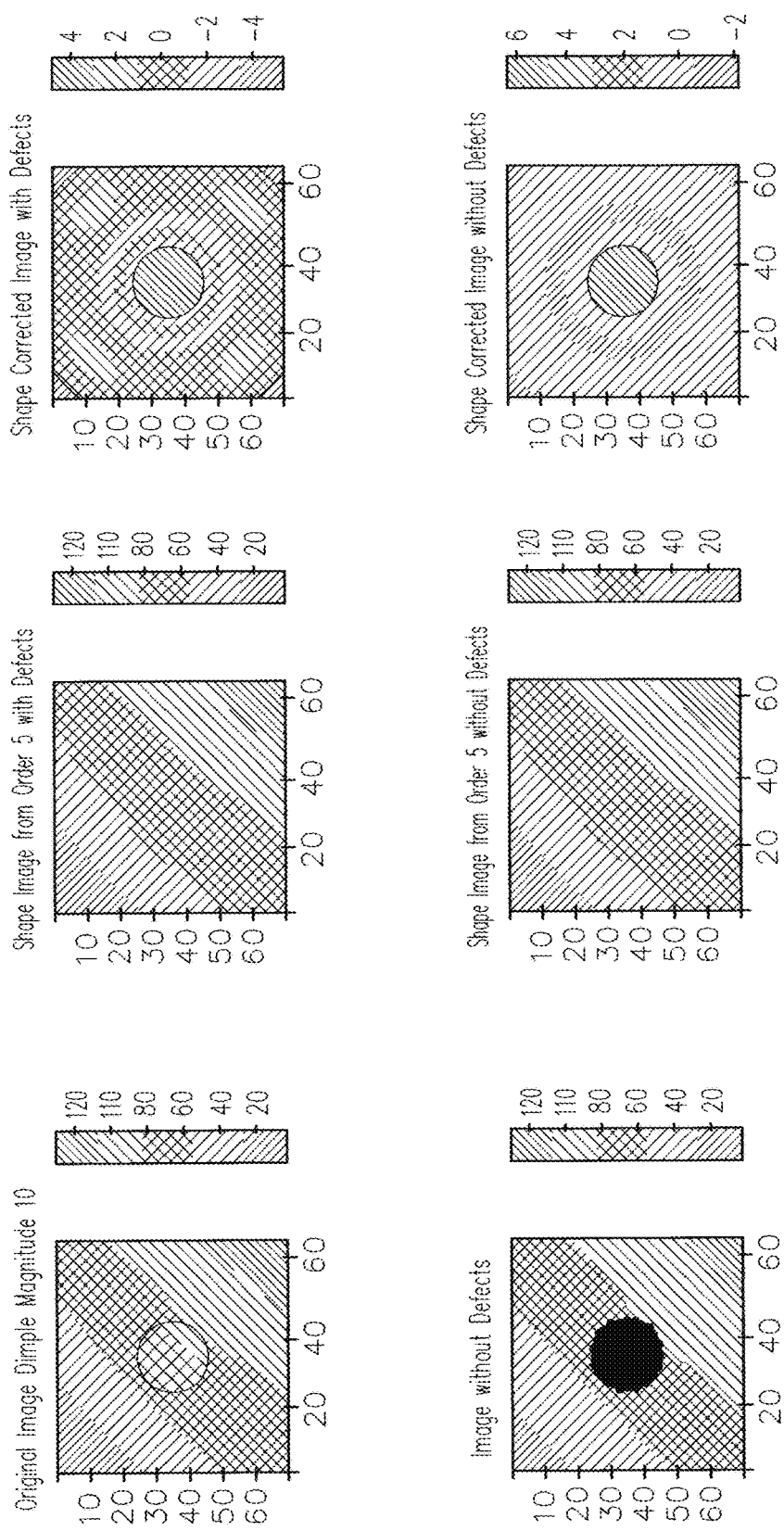
FIG. 16 illustrates a surface fitting testing result performed with the defect pixels included compared against a surface fitting testing result performed without the defect pixels.

It is contemplated that any surface fitting algorithms may be utilized without departing from the scope and spirit of the present disclosure. However, it is very important to exclude the defect pixels in the surface fitting in order to obtain more accurate defect quantification. When fitting with the defect pixels included, the calculated area surface will be biased by the defects, especially when the defect has high magnitude and large area. This has been observed in various testing samples, including the one demonstrated in FIG. 16. In this example, a Gaussian shaped defect with 10 nm height is modeled. When the defect pixels are used in the surface fitting, the estimated defect height is 4.3 nm. When the defect pixels are excluded in the surface fitting, the estimated defect height is 6.3 nm, closer to the accurate defect height value.

As previously mentioned, for long extent defects, such as a long scratch 1516 as illustrated in FIG. 15D, the measurement may be carried out in a scanning mode, with a measurement window 1514 moving along the scratch trace automatically guided by the defect pixel positions. In this scanning mode, a sequence of "focal" image areas covering the long scratch is defined and the surface fittings over these areas are performed. The required defect height and depth values from each area are calculated and then aggregated to form the maximum height and depth values of the complete scratch according to equation:

$$P_{complete} = \max_i [P_1, P_2, \ldots, P_i, \ldots, P_n]$$

$$V_{complete} = \min_i [V_1, V_2, \ldots, V_i, \ldots, V_n]$$

where $P_i$ and $V_i$ are the peak and valley values calculated from $i_{th}$ window and there are a total n measurement windows in the scanning trace. Other information for the complete scratch can be obtained similarly.

Figure 17:
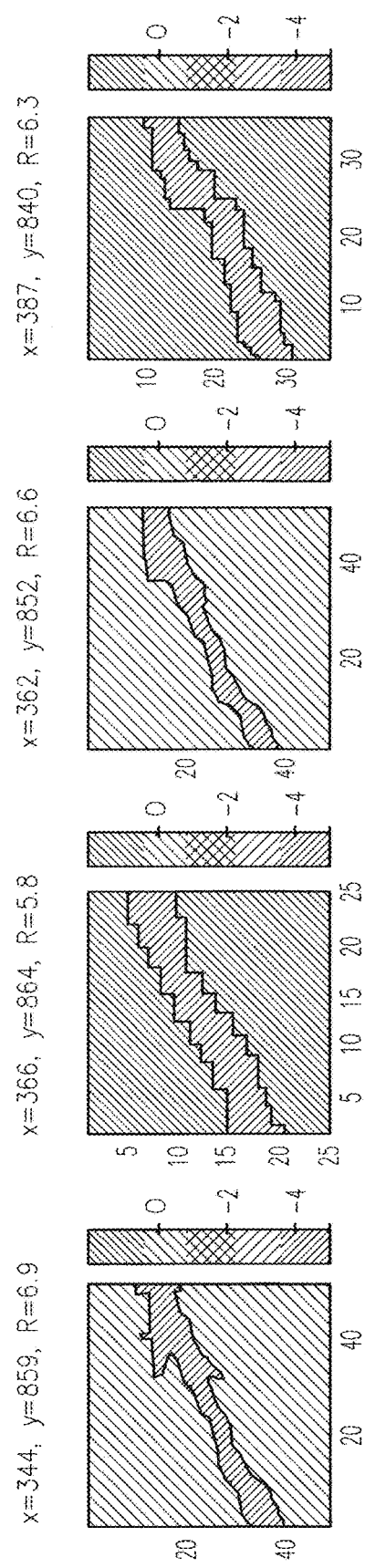
FIG. 17 illustrates areas in the scanning sequence for an exemplary long scratch.

Some areas in the scanning sequence for an exemplary long scratch are shown in FIG. 17. When performing the surface fitting for the long scratch, unlike the compact defect such as dimple and EPI crowns where the defect pixel positions will not touch the area boundary, the defect pixel positions will cross the area boundary (as depicted in FIG. 15D). However, since the scratch usually only occupies a small part of the image area, there are still enough non-defect pixels for the accurate reference surface estimate, even if all defect pixels are masked off in the surface fitting, providing accurate maximum scratch depth calculation.

As previously mentioned, the ability to measure the feature height, depth, area and volume using the robust surface fitting on the original surface image areas in step 110 (and step 212) allows method 100 (and method 200) to provide valuable information, including defect volume information, for wafer production.

While the examples above illustrate utilizing the system and method in accordance with the present disclosure for surface defect detection, classification and quantification of bare wafers and patterned wafers, it is contemplated that the system and method in accordance with the present disclosure are also applicable for the defect detection in filmed wafer applications. Similar to the handling of patterned wafers, certain additional data processing stages, such as film response calibration and compensation, may be performed to reduce the signal variation from different film materials and film structures so that the processed signals can better represent the wafer surface height information. Subsequently, the detection, classification and quantification steps as described above may be carried out for such filmed wafers.

Furthermore, while method 100 (and method 200) in accordance with the present disclosure may be utilized with most optical systems (e.g., wafer geometry metrology tools and interferometer systems), it is contemplated that such techniques may provide improved accuracies when utilized with certain interferometer systems that are capable of providing accurate wafer surface height information. For instance, wafer dimensional geometry tools, such as the WaferSight metrology tool, can provide wafer surface height information with accuracy in nanometers and thus can provide very accurate results in inspection and classification.

Since the measurements from such wafer dimensional geometry tools provide information about defect polarities, such data can be utilized to identify a defect as protrusion, such as a bump, or intrusion, such as a pit. Combining such data with the defect height profile and area information, the shape of the defects in 3D may be defined and the defect volume information may be calculated. The height, volume and 3D shape information of defects are very helpful in the defect classification and reduction of the irrelevant or false defects in the wafer inspection and classification. It helps defining lower thresholds to achieve more sensitive detection of the defects of interests, without generating unmanageable false or irrelevant defects.

Figure 18:
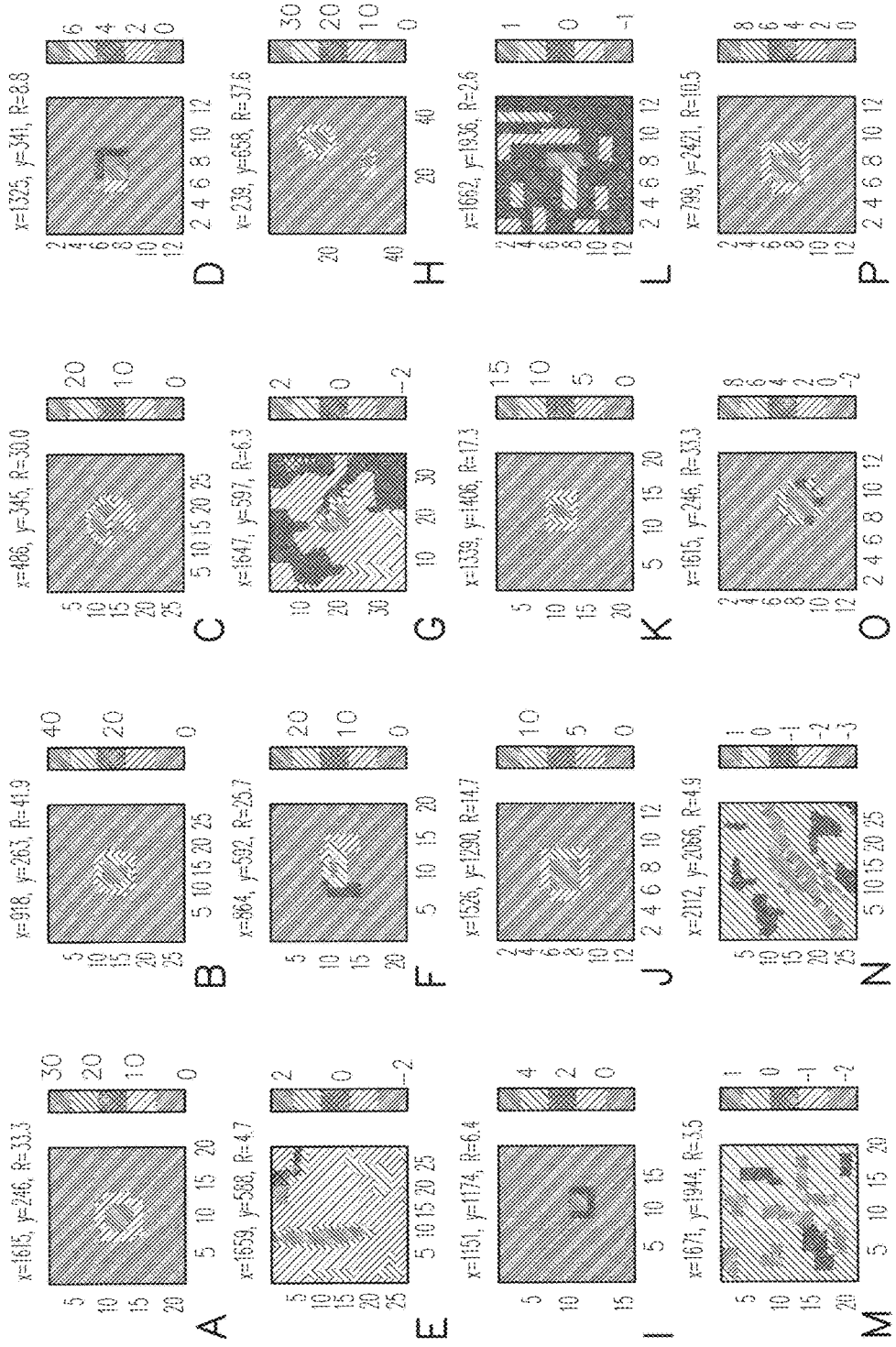
FIG. 18 illustrates utilizing defect height information for eliminating weak defects.

For example, since the defect height information is available, it can be utilized to remove irrelevant defects and improve the detection purity level. As shown in FIG. 18, using the defect height/depth magnitude information, several weak defects such as 18E, 18G, 18L, 18M and 18N may be eliminated from the final reporting. In addition, the defect signal polarity obtained from the quantification can also be helpful to classify the defects. For example, the scratch is a structure into the wafer surface and therefore the negative height value will be reported to improve the scratch defect classification accuracy.

Another unique capability provided by the WaferSight (other wafer dimensional geometry tools) based inspection, classification and quantification system is that it can provide valuable defect volume information. From the calculated defect height surface with the adaptive robust surface fitting, the volumes of the detected defects can be calculated by integrating the height values over the defect area defined by the defect positions. The integration can use the absolute defect height values for the volume constructed by the defect surface with the reference surface. Alternatively, the defect volumes can be calculated separately from the positive defect pixels and the negative pixels to get two components. As shown in FIG. 19, the defect volume information can describe the defect in one more important dimension, in addition to the defect height and area information. For example, in integrated circuit manufacturing, how much material is missing or extra from the defects may be of a particular concern. The two defects illustrated in FIG. 19 may have the same heights, the same areas but very different volumes. This volume information may indicate how much material is missing or extra, and is also useful for defect type classification.

It is contemplated that while the examples above referred to wafer inspections, the systems and methods in accordance with the present disclosure are applicable to other types of polished plates as well without departing from the spirit and scope of the present disclosure. The term wafer used in the present disclosure may include a thin slice of semiconductor material used in the fabrication of integrated circuits and other devices, as well as other thin polished plates such as magnetic disc substrates, gauge blocks and the like.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:
1. A method for inspecting a wafer, comprising:
setting up a data acquisition and a data processing recipe;
acquiring a wafer surface image utilizing an optical system, the optical system configured for acquiring the wafer surface image by obtaining at least one intensity frame of at least a front surface or a back surface of a wafer, the optical system including at least one of a wafer geometry tool or an interferometer tool;
filtering the wafer surface image to increase signal to background contrast;

performing wafer edge treatment to suppress strong filter response;

performing defect detection and classification based on the filtered wafer surface image;

calculating at least one of: a height, a depth, a surface area, or a volume of the defect, the at least one of: the height, the depth, the surface area, or the volume being calculated by:

calculating a mass center of the defect and a maximum distance of the defect pixels to the mass center;

defining an image area based on the mass center and the maximum distance;

obtaining a fitted surface profile for the image area by performing surface fitting for the image area; and calculating at least one of: the height, the depth, the surface area, or the volume of the defect based on the fitted surface profile for the image area;

defining one or more wafer inspection thresholds to increase a detection purity level for a wafer inspection process in a semiconductor device production process based on the at least one of: the height, the depth, the surface area, or the volume of the defect detected and classified; and providing one or more control signals based on the at least one of: the height, the depth, the surface area, the volume of the defect detected and classified, or the defined one or more wafer inspection thresholds to a semiconductor fabrication process tool to control a semiconductor fabrication process in the semiconductor device production process.

2. The method of claim 1, wherein the step of performing defect detection and classification is configured for detection and classification of edge crowns, said step further comprises:

forming a two-dimensional radius-size histogram based on radius positions and sizes in pixels of detected edge crowns in the wafer surface image;

smoothing the two-dimensional radius-size histogram and identifying a peak position of the smoothed radius-size histogram;

estimating a defect radius and a defect size based on the peak position of the smoothed radius-size histogram;

estimating an angular separation of the detected edge crowns; and sifting the detected edge crowns based on the estimated defect radius, the estimated defect size, and the estimated angular separation.

3. The method of claim 1, wherein the step of performing defect detection and classification is configured for detection and classification of scratches, said step further comprises:

filtering the wafer surface image to remove low frequency surface shape components;

obtaining a binary defect map by applying an intensity threshold to the filtered wafer surface image; and applying a line enhancement technique to the binary defect map to connect broken scratch data points and remove other isolated defect points.

4. The method of claim 1, wherein the step of performing defect detection and classification is configured for detection and classification of sliplines, said step further comprises:

partitioning the wafer surface to different regions based on wafer crystal structure orientation; and applying a line enhancement technique for each particular region, wherein the direction of the line enhancement is based on the crystal structure orientation of the particular region.

5. The method of claim 1, wherein the step of performing defect detection and classification is configured for detection and classification of sliplines, said step further comprises:

identifying a plurality of defect objects in the wafer surface image;

obtaining a binary defect map for each of the plurality of defect objects;

calculating a histogram of oriented gradients (HOG) for each of the plurality of defect objects based on its corresponding binary defect map; and detecting and classifying each of the plurality of defect objects based on its corresponding HOG.

6. The method of claim 1, wherein the step of calculating at least one of: the height, the depth, the surface area, or the volume of the defect further comprises:

obtaining the fitted surface profile for an image area by performing surface fitting for the image area of the wafer surface image, wherein pixels in the defect are excluded from the surface fitting process;

estimating a defect surface profile based on a difference between an original surface profile and the fitted surface profile; and calculating at least one of: the height, the depth, the surface area, or the volume of the defect based on the defect surface profile.

7. The method of claim 1, wherein the step of calculating at least one of: the height, the depth, the surface area, or the volume of the defect further comprises:

defining a plurality of measurement windows along a scanning trace;

calculating at least one of: the height, the depth, the surface area, or the volume of the defect within each of the plurality of measurement windows utilizing surface fitting; and aggregating the calculated values of each of the plurality of measurement windows to form said at least one of: the height, the depth, the surface area, or the volume of the defect.

8. A method for inspecting a wafer, comprising:

setting up a data acquisition and a data processing recipe;

acquiring a wafer surface image utilizing an optical system, the optical system configured for acquiring the wafer surface image by obtaining at least one intensity frame of at least a front surface or a back surface of a wafer, the optical system including at least one of a wafer geometry tool or an interferometer tool;

performing data processing for a patterned wafer surface, including at least one of:

correcting wafer XY distortions to obtain uniform patterns;

generating a reference wafer and aligning the wafer under operation to the reference wafer; or performing wafer-to-wafer operations to suppress the pattern signal and produce residue wafer surface images;

filtering the wafer surface image to increase signal to background contrast;

performing defect detection and classification based on the filtered wafer surface image;

calculating at least one of: a height, a depth, a surface area, or a volume of the defect by:

calculating a mass center of the defect and a maximum distance of the defect pixels to the mass center;

defining an image area based on the mass center and the maximum distance;

obtaining a fitted surface profile for the image area by performing surface fitting for the image area; and calculating at least one of: the height, the depth, the surface area, or the volume of the defect based on the fitted surface profile for the image area;

defining one or more wafer inspection thresholds to increase a detection purity level for a wafer inspection process in a semiconductor device production process based on the at least one of: the height, the depth, the surface area, or the volume of the defect detected and classified; and providing one or more control signals based on the at least one of: the height, the depth, the surface area, the volume of the defect detected and classified, or the defined one or more wafer inspection thresholds to a semiconductor fabrication process tool to control a semiconductor fabrication process in the semiconductor device production process.

9. The method of claim 8, wherein the step of performing defect detection and classification is configured for detection and classification of edge crowns, said step further comprises:

forming a two-dimensional radius-size histogram based on radius positions and sizes in pixels of detected edge crowns in the wafer surface image;

smoothing the two-dimensional radius-size histogram and identifying a peak position of the smoothed radius-size histogram;

estimating a defect radius and a defect size based on the peak position of the smoothed radius-size histogram;

estimating an angular separation of the detected edge crowns; and sifting the detected edge crowns based on the estimated defect radius, the estimated defect size, and the estimated angular separation.

10. The method of claim 8, wherein the step of performing defect detection and classification is configured for detection and classification of scratches, said step further comprises:

filtering the wafer surface image to remove low frequency surface shape components;

obtaining a binary defect map by applying an intensity threshold to the filtered wafer surface image; and applying a line enhancement technique to the binary defect map to connect broken scratch data points and remove other isolated defect points.

11. The method of claim 8, wherein the step of performing defect detection and classification is configured for detection and classification of sliplines, said step further comprises:

partitioning the wafer surface to different regions based on wafer crystal structure orientation; and applying a line enhancement technique for each particular region, wherein the direction of the line enhancement is based on the crystal structure orientation of the particular region.

12. The method of claim 8, wherein the step of performing defect detection and classification is configured for detection and classification of sliplines, said step further comprises:

identifying a plurality of defect objects in the wafer surface image;

obtaining a binary defect map for each of the plurality of defect objects;

calculating a histogram of oriented gradients (HOG) for each of the plurality of defect objects based on its corresponding binary defect map; and detecting and classifying each of the plurality of defect objects based on its corresponding HOG.

13. The method of claim 8, wherein the step of calculating at least one of: the height, the depth, the surface area, or the volume of the defect further comprises:

obtaining the fitted surface profile for an image area by performing surface fitting for the image area of the wafer surface image, wherein pixels in the defect are excluded from the surface fitting process;

estimating a defect surface profile based on a difference between an original surface profile and the fitted surface profile; and calculating at least one of: the height, the depth, the surface area, or the volume of the defect based on the defect surface profile.

14. The method of claim 8, wherein the step of calculating at least one of: the height, the depth, the surface area, or the volume of the defect further comprises:

defining a plurality of measurement windows along a scanning trace;

calculating at least one of: the height, the depth, the surface area, or the volume of the defect within each of the plurality of measurement windows utilizing surface fitting; and aggregating the calculated values of each of the plurality of measurement windows to form said at least one of: the height, the depth, the surface area, or the volume of the defect.

15. A wafer inspection system, comprising:

an optical system, the optical system configured for acquiring a wafer surface image by obtaining at least one intensity frame of at least a front surface or a back surface of a wafer, the optical system including at least one of a wafer geometry tool or an interferometer tool;

a processor in communication with the optical system, the processor configured for performing wafer surface feature detection, classification and quantification, said wafer surface feature detection, classification and quantification including:

filtering the wafer surface image to increase signal to background contrast;

performing wafer edge treatment to suppress strong filter response;

performing defect detection and classification based on the filtered wafer surface image;

calculating at least one of: a height, a depth, a surface area, or a volume of the defect by:

calculating a mass center of the defect and a maximum distance of the defect pixels to the mass center;

defining an image area based on the mass center and the maximum distance;

obtaining a fitted surface profile for the image area by performing surface fitting for the image area; and calculating at least one of: the height, the depth, the surface area, or the volume of the defect based on the fitted surface profile for the image area;

defining one or more wafer inspection thresholds to increase a detection purity level for a wafer inspection process in a semiconductor device production process based on the at least one of: the height, the depth, the surface area, or the volume of the defect detected and classified; and providing one or more control signals based on the at least one of: the height, the depth, the surface area, the volume of the defect detected and classified, or the defined one or more wafer inspection thresholds to a semiconductor fabrication process tool to control a semiconductor fabrication process in the semiconductor device production process; and a display device configured to display the at least one of: the height, the depth, the surface area, or the volume of the defect detected and classified.

16. The system of claim 15, wherein the system is configured for inspecting a bare wafer, and wherein the processor is configured for performing wafer edge treatment to suppress strong filter response prior to performing defect detection and classification based on the filtered wafer surface image.

17. The system of claim 15, wherein the system is configured for inspecting a patterned wafer, and wherein the processor is configured for performing data processing for the patterned wafer surface, including at least one of:
   correcting wafer XY distortions to obtain uniform patterns;
   generating a reference wafer and aligning the wafer under operation to the reference wafer; or
   performing wafer-to-wafer operations to suppress the pattern signal and produce residue wafer surface images.

18. The system of claim 15, wherein the system is configured for inspecting a filmed wafer, and wherein the processor is configured for performing film response calibration and compensation for the filmed wafer surface to reduce signal variations from different film materials and film structures.

19. The system of claim 15, wherein the system is configured for detection and classification of edge crowns, and wherein the processor is configured for:
   forming a two-dimensional radius-size histogram based on radius positions and sizes in pixels of detected edge crowns in the wafer surface image;
   smoothing the two-dimensional radius-size histogram and identifying a peak position of the smoothed radius-size histogram;
   estimating a defect radius and a defect size based on the peak position of the smoothed radius-size histogram;
   estimating an angular separation of the detected edge crowns; and
   sifting the detected edge crowns based on the estimated defect radius, the estimated defect size, and the estimated angular separation.

20. The system of claim 15, wherein the system is configured for detection and classification of scratches, and wherein the processor is configured for:
   filtering the wafer surface image to remove low frequency surface shape components;
   obtaining a binary defect map by applying an intensity threshold to the filtered wafer surface image; and
   applying a line enhancement technique to the binary defect map to connect broken scratch data points and remove other isolated defect points.

21. The system of claim 15, wherein the system is configured for detection and classification of sliplines, and wherein the processor is configured for:
   partitioning the wafer surface to different regions based on wafer crystal structure orientation; and
   applying a line enhancement technique for each particular region, wherein the direction of the line enhancement is based on the crystal structure orientation of the particular region.

22. The system of claim 15, wherein the system is configured for detection and classification of sliplines, and wherein the processor is configured for:
   identifying a plurality of defect objects in the wafer surface image;
   obtaining a binary defect map for each of the plurality of defect objects;
   calculating a histogram of oriented gradients (HOG) for each of the plurality of defect objects based on its corresponding binary defect map; and
   detecting and classifying each of the plurality of defect objects based on its corresponding HOG.

23. The system of claim 15, wherein calculating at least one of: the height, the depth, the surface area, or the volume of the defect further comprises:
   obtaining the fitted surface profile for an image area by performing surface fitting for the image area of the wafer surface image, wherein pixels in the defect are excluded from the surface fitting process;
   estimating a defect surface profile based on a difference between an original surface profile and the fitted surface profile; and
   calculating at least one of: the height, the depth, the surface area, or the volume of the defect based on the defect surface profile.

24. The system of claim 15, wherein calculating at least one of: the height, the depth, the surface area, or the volume of the defect further comprises:
   defining a plurality of measurement windows along a scanning trace;
   calculating at least one of: the height, the depth, the surface area, or the volume of the defect within each of the plurality of measurement windows utilizing surface fitting; and
   aggregating the calculated values of each of the plurality of measurement windows to form said at least one of: the height, the depth, the surface area, or the volume of the defect.

25. The system of claim 15, wherein the optical system is configured for providing wafer surface height information.

* * * * *